United States Patent [19]

Miyahara et al.

[11] Patent Number: 4,503,552
[45] Date of Patent: Mar. 5, 1985

[54] SIMPLE MOUNTING STRUCTURE FOR DENTAL X-RAY APPARATUS

[75] Inventors: Masato Miyahara, Otsu; Michiaki Okano, Uji; Daryl R. Beach, Atami, all of Japan

[73] Assignee: Kabushiki Kaisha Morita Seisakusho, Kyoto, Japan

[21] Appl. No.: 449,740

[22] Filed: Dec. 14, 1982

[30] Foreign Application Priority Data

Dec. 15, 1981 [JP] Japan .......................... 56-187254[U]
Dec. 17, 1981 [JP] Japan .......................... 56-189244[U]

[51] Int. Cl.³ .......................... A61B 6/14; A61B 6/04
[52] U.S. Cl. .......................... 378/196; 378/197
[58] Field of Search ............... 378/196, 197, 198, 195, 378/193

[56] References Cited

U.S. PATENT DOCUMENTS 2,668,912  2/1954  Goldfield et al. ................. 378/197
2,849,620  8/1958  Koerner .............................. 378/197
2,909,665  10/1959 Guentner et al. .................. 378/197

Primary Examiner—Alfred E. Smith
Assistant Examiner—T. N. Grigsby
Attorney, Agent, or Firm—Koda and Androlia

[57] ABSTRACT

This disclosure relates to a simple mounting structure for a dental X-ray apparatus. The structure is used in combination with a substantially horizontal treatment bed in such manner that irradiation tube of an X-ray head is designed to take a correct position with respect to the mouth region of a patient lying on the treatment bed with his head resting on the headrest of the bed. The structure includes the treatment bed, an X-ray head support connected to one side of the bed and made up of an assembly of a plurality of hollow tubes adjustable in length in the three-dimensional directions of length, width and height of the bed and an X-ray head mounted at the end of the support and swingable in a back-and-forth direction with respect to an axis of the irradiation tube. The irradiation tube is mounted on the X-ray head and movable toward and away from the mouth region. The structure permits simple and correct positioning of the X-ray apparatus with respect to a patient lying on the bed.

10 Claims, 10 Drawing Figures

SIMPLE MOUNTING STRUCTURE FOR DENTAL X-RAY APPARATUS

BACKGROUND OF THE INVENTION

1. Field of the Invention

This invention relates to a structure for simply mounting a dental X-ray apparatus to a dental treatment bed, and more particularly to a structure for simply mounting a dental X-ray apparatus capable of easily and correctly positioning an X-ray tube in three-dimensional directions with respect to the mouth region of a patient placed in a specified position on a headrest of the treatment bed.

2. Prior Art

Heretofore, dental X-ray photography has not only had certain disadvantages in that, because it has not employed in a treatment system under which a patient is placed in his supine position on the treatment bed, the photography was lacking in correctness but has also had a problem in that, partly because an arm with a balancing rod was used for moving and selecting an X-ray photographing position, the photographing position of the patient was selected by freely operating the balancing rod, so that correct reproduction of the photographing position was impossible. Especially, in an apparatus for use in dental training, it was impposible to make it numerically clear for an instructor and a trainee to select the photographing position.

From this fact it has been a desire to create a structure capable of correctly positioning an X-ray apparatus in relation with a treatment bed. On the other hand, in group medical examination schools and in the remote local areas of the country, there has been introduced a special medical examination car equipped with a treatment bed and X-ray apparatus; but in doctorless villages in the out-of-the-way areas where there is little or no traffic of cars, it is often the case wherein people cannot avail themselves of the X-ray apparatus and treatment chairs or tables placed in a medical car. Besides, expense for buying and maintaining such special cars is also large, which fact has been a problem in the expansion and improvement of health services, such as early findings and treatment of decayed teeth and straightening of irregular teeth. From this viewpoint, it also has been a desire to simplify the assembling and disassembling of a mounting structure in an X-ray apparatus and to make the structure light in weight.

SUMMARY OF THE INVENTION

In view of the above, this invention has for its main object the provision of an X-ray apparatus capable of taking correct photographing by simple operation and particularly capable of correctly reproducing the photographing position of a patient.

The invention has for another object the provision of an easy-to-mount structure of a dental X-ray apparatus which is simple to assemble and disassemble, light in weight, convenient for carriage and strong in finished assembly. Preferred embodiments of the invention are of the construction wherein, when an X-ray photograph is not taken, the X-ray head and support can be collapsed and stored in one side portion of the treatment bed assembly so as not to impede dental treatment activities.

Two preferred embodiments of the invention will now be described with reference to the accompanying drawings.

DETAILED DESCRIPTION OF THE INVENTION

Figure 1:
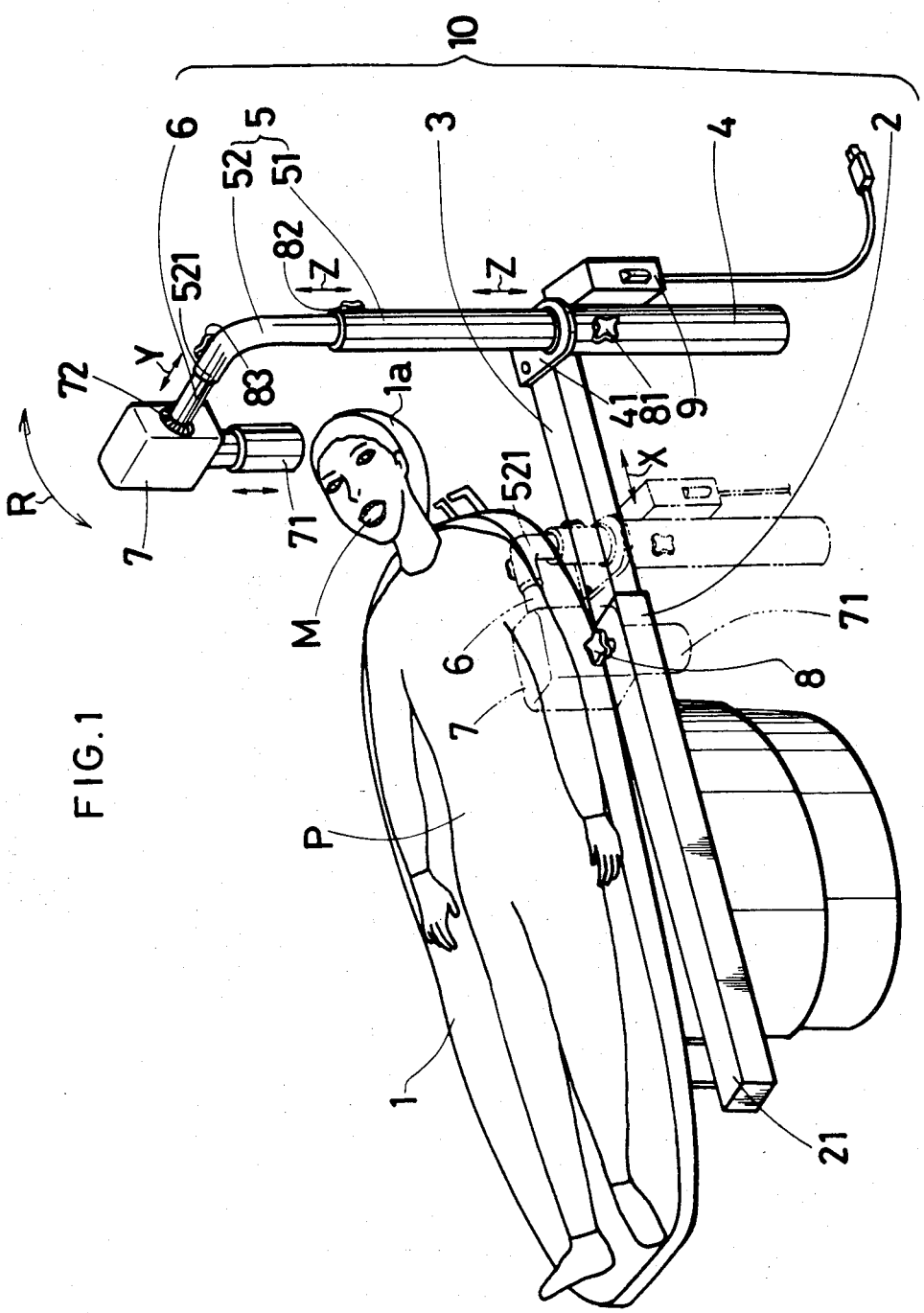
FIG. 1 is a perspective view showing the structure of a first embodiment of the invention when in use.

The structure of the invention common to the two embodiments thereof is that an irradiation tube 71 of an X-ray head 7 is mounted in combination with a substantially horizontal treatment bed 1 so that the tube 71 is held in a specified position with respect to the mouth region M of a patient P lying on his back on the bed 1 with his head on the headrest 1a of the bed. The apparatus of the invention includes the treatment bed 1, an X-ray head support 10 connected to one side of the bed 1 and made up of an assembly of a plurality of hollow tubes adjustable in length in the three-dimensional directions of length X, width Y and height Z of the head 1, an X-ray head 7 mounted at the end of the support 10 and swingable in a back-and-forth direction R with respect to an axis of the X-ray tube 71, and the X-ray tube 71 mounted on the X-ray head 7 and movable toward and away from the mouth region M.

The first embodiment is different from a second embodiment in that the former is of an installation type capable of collapsibly storing the X-ray head 7 and the support 10 in one side of the treatment bed 1, while the latter is of a demountable and portable type wherein the support 10 may be assembled and disassembled on the site.

Referring now to the structure of the first embodiment of the invention with references to FIGS. 1 and 3, the invention includes a storing track 2 having the support 10 fixed to the end thereof and mounted horizontally on one side of the treatment bed 1 along the longitudinal direction X of the bed 1, a slider 3 slidably inserted into the track 2 in the longitudinal direction X, a stand pole telescopable tube 4 connected in a vertical direction Z to the end of the slider 3, a stand pole 5 inserted into the telescopable tube 4 which is vertically slidable and movable around the axis of the tube 4 and having a horizontally curved portion 521 on the top thereof, and an operating tube 6 fitted into the curved portion 521 which is slidable in the direction of width Y, whereby the X-ray head 7 is mounted to the operating tube 6. When the tube 6 and the pole 5 are telescoped into the stand pole telescopable tube 4 and when the slider 3 is telescoped into the storing track 2, the X-ray head 7 and support 10 are telescoped into one side of the treatment bed 1. The storing track 2 fixed parallelly and horizontally to one side of a support frame of the treatment bed in the longitudinal direction of the head X of the head 1 has a slider 3 mounted slidably in a horizontal and longitudinal direction X by a slidable guide mechanism (not shown) using a linear rotary bearing which is available under the tradename of "LINEAR WAY", and has a stopper 8 for locking the slider 3 in a suitable position on the upper portion 21 of the stopper 8. The slider 3 and track 2 are square hollow pillars. A stand pole telescopable tube 4 is fixedly connected to the end side of the slider 3 through a horizontal connector 41 in the direction of height, namely in a vertical direction. The stand pole telescopable tube 4 forms a hollow cylindrical shape in the embodiment shown, and in the cavity of the tube 4 is incorporated a slider guide mechanism (not shown) such as the above described linear rotary bearing so as to slidably store a standpole 5 in a vertical direction Z and includes a screw stopper 81 for locking the standpole 5 in a suitable position and a control box 9 for operating the X-ray photographing on the outside of the pole 5. The stand pole 5 includes a curved portion 521 extending curvedly and horizontally in the direction of width Y on the top of the pole 5. In this case, one cylindrical stand pole having the curved portion 521 on the top of the pole 5 may be used, but the embodiment shown is assembled in the manner that a separate curved pole 52 having a curved portion 521 is fitted into a vertical pole 51 which is vertically slidable and rotatable with respect to each other around the axes of the poles 52 and 51 and is fixed by a stopper 82 so as to make up for a shortage in the rise of the stand pole 5. Into the end of this curved portion 521 is inserted a control tube, and an X-ray tube head 7 having an expansible irradiation tube 71 is rotatably supported (normally limited so as to permit swing at an angle of 45° in a back-and-forth direction R with respect to the axis of the irradiation tube 71, i.e. around the axis of the operating tube 6 through a swing angle indicating dial 72), and a screw stopper 83 for fixing the tube 6 at a suitable position to the curved pole 52 is provided on the laterial side of the curved pole 52. A fine slide guide mechanism (not shown) of the the type described above is incorporated also into the slide and rotational elements.

Figure 2:
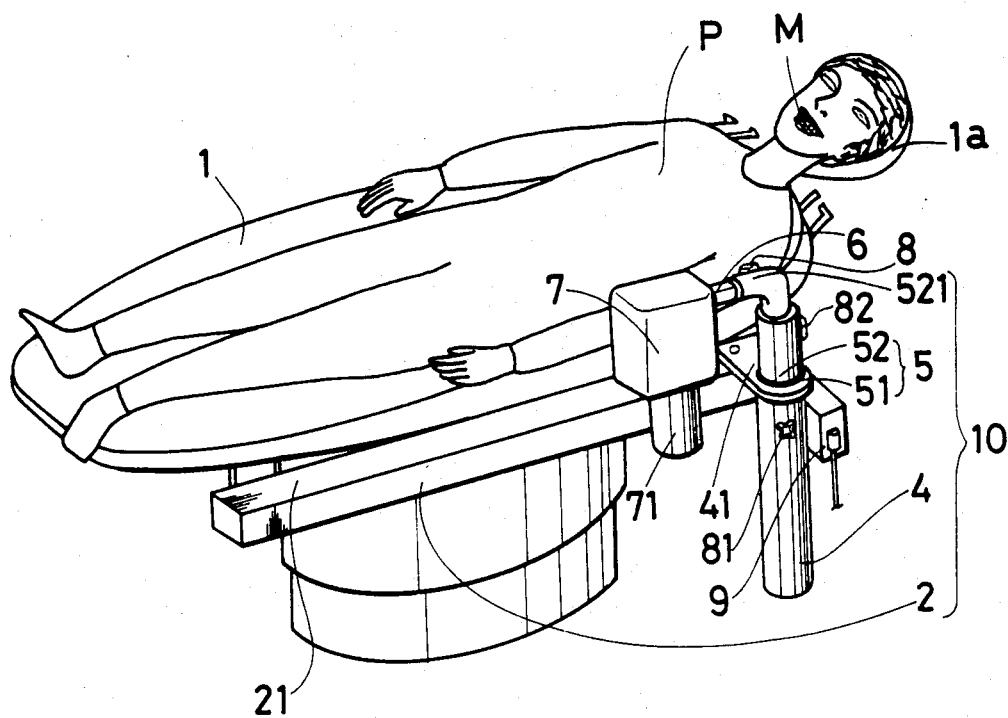
FIG. 2 is a perspective view showing the structure of the embodiment in its stored state.
Figure 3A:
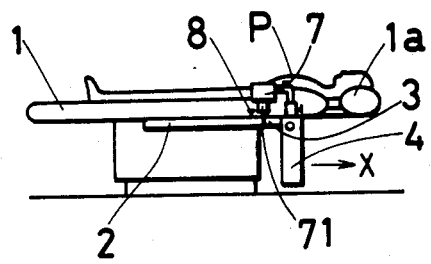
FIG. 3(a) is a diagrammatic view illustrating the state of the structure prior to a first step for its assembling from its stored state.
Figure 3B:
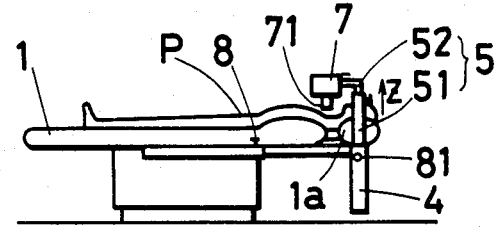
FIG. 3(b) is a diagrammatic view illustrating the state of the structure after the first and a second step for its assembling has been completed.
Figure 3C:
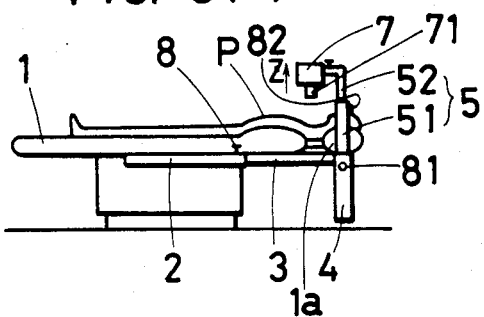
FIG. 3(c) is a diagrammatic view illustrating the state of the structure after a third step for its assembling has been completed.
Figure 3D:
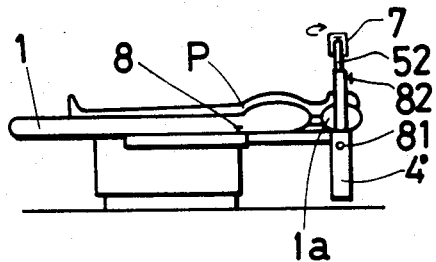
FIG. 3(d) is a diagrammatic view illustrating the state of the structure prior to a fifth step but after the fourth step for its assembling has been completed.
Figure 3E:
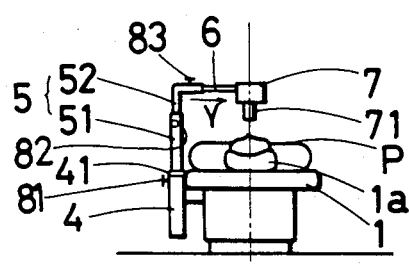
FIG. 3(e) is a diagrammatic view illustrating the state of the structure after the fifth step has been completed.

Referring to the apparatus of the invention with the construction described above, and more particularly to a procedure for assembling the apparatus from the collapsed in FIG. 2 in which the X-ray head 7 and support 10 are shown collapsed to the state of use in FIG. 1 in which the same is shown assembled for use, a first step, as shown by an arrow in FIG. 3(a), is to slide the stand pole telescopable tube 4 in the longitudinal direction X of the bed 1 and set the tube 4 in a position in the neighborhood of the mouth region M of a patient and lock the slider 3 by means of a screw stopper 8. A second step, as shown in FIG. 3(b), is to slide the vertical pole 51 in the direction of height Z and lock the pole 51 at the highest position by a screw stopper 81. Thereafter a third step, as shown in FIG. 3(c), is to lift the curved pole 52 so as to make up for a shortage in lift. Thereafter a fourth step, as shown in FIG. 3(d), is to rotate the X-ray head 7 through an angle of about 90° and fix the head 7 by a screw stopper 82. Thereafter, a fifth step, as shown in FIG. 3(e), is to slide the operating tube 6 as far as the X-ray head 7 reaches a median lines of a patient in the direction of width Y and to fix the operating tube 6 by a screw stopper 83. The ultimate distance between the focus and the skin is controlled by adjusting the length of the expansible irradiation tube 71 like a microscope. In the steps above, either of the FIGS. 3(c) and 3(e) steps precede in order. Conversely, when it is desired to collapse the apparatus from the state of use shown in FIG. 1 to the state of storage shown in FIG. 2, it is only necessary to reverse the assembling procedures mentioned above. In the embodiment illustrated, it is to be understood that a system of positioning the irradiation tube 71 in the three-dimensional directions of the coordinate axes X, Y and Z belongs to the embodiment illustrated. But the position of the irradiation tube 71 according to a polar coordinate system, namely a system of positioning the irradiation tube 71 by the length and angle of a hollow tube constituting the support 10 may also be included in this embodiment.

As described above, since in the structure of the embodiment the X-ray head 7 is supported by the support 10 so that the irradiation tube 71 of the X-ray head may be transferred so as to freely adjust the position thereof with respect to the mouth region M of a patient whose head is placed on the headrest 1a of the bed 1, there is no necessity for moving the patient P from the bed 1 to an X-ray room and the positioning of the irradiation tube and reproduction of the positioning can be carried out numerically, correctly and positively. In addition, because a hollow structure is used as a support, a light weight frame can be provided with comparatively simple operation. Furthermore, separation of the stand pole 5 and operation tube 6 from the slider 3 makes it possible to carry the pole and tube independently of the bed 1 and reassemble the same into a complete set on the site. This is an advantage. In the first embodiment, since the X-ray head 7 and support 10 are telescoped into one side of the bed 1, the invention provides another advantage that, when not in use, the head 7 and the support 10 can compactly be telescoped into one side of the bed so as not to obstruct treatment activities.

Figure 4:
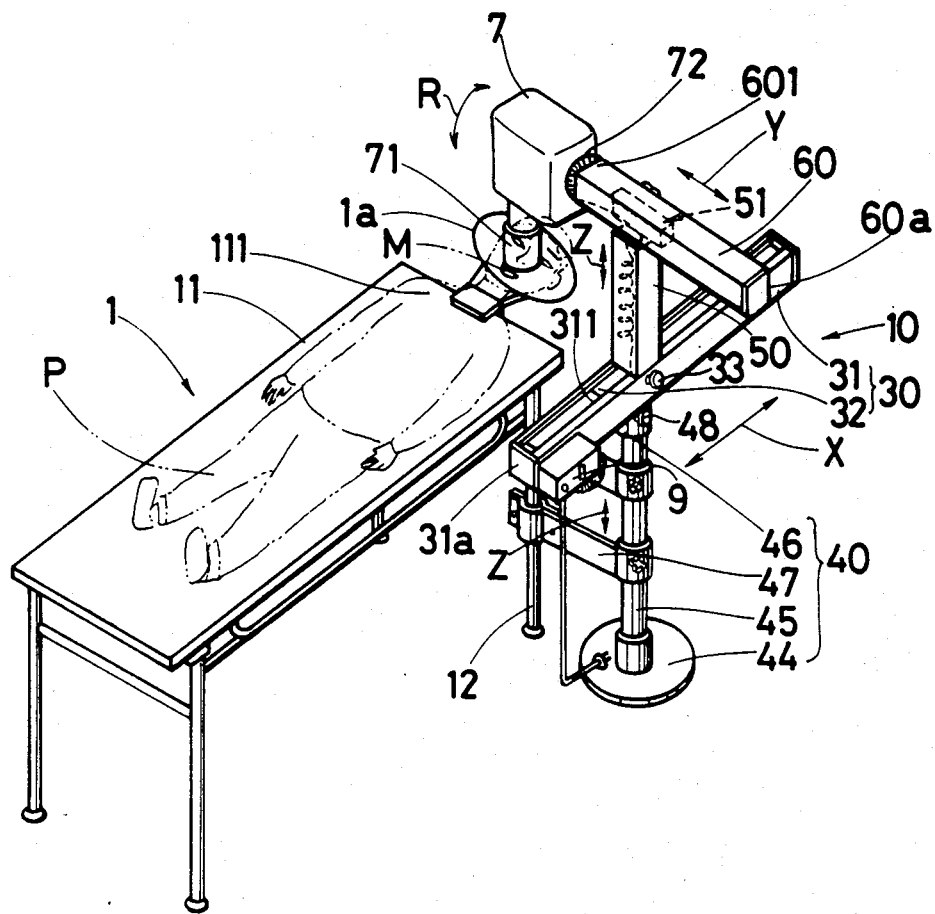
FIG. 4 is a perspective view of a second embodiment of the invention.
Figure 6:
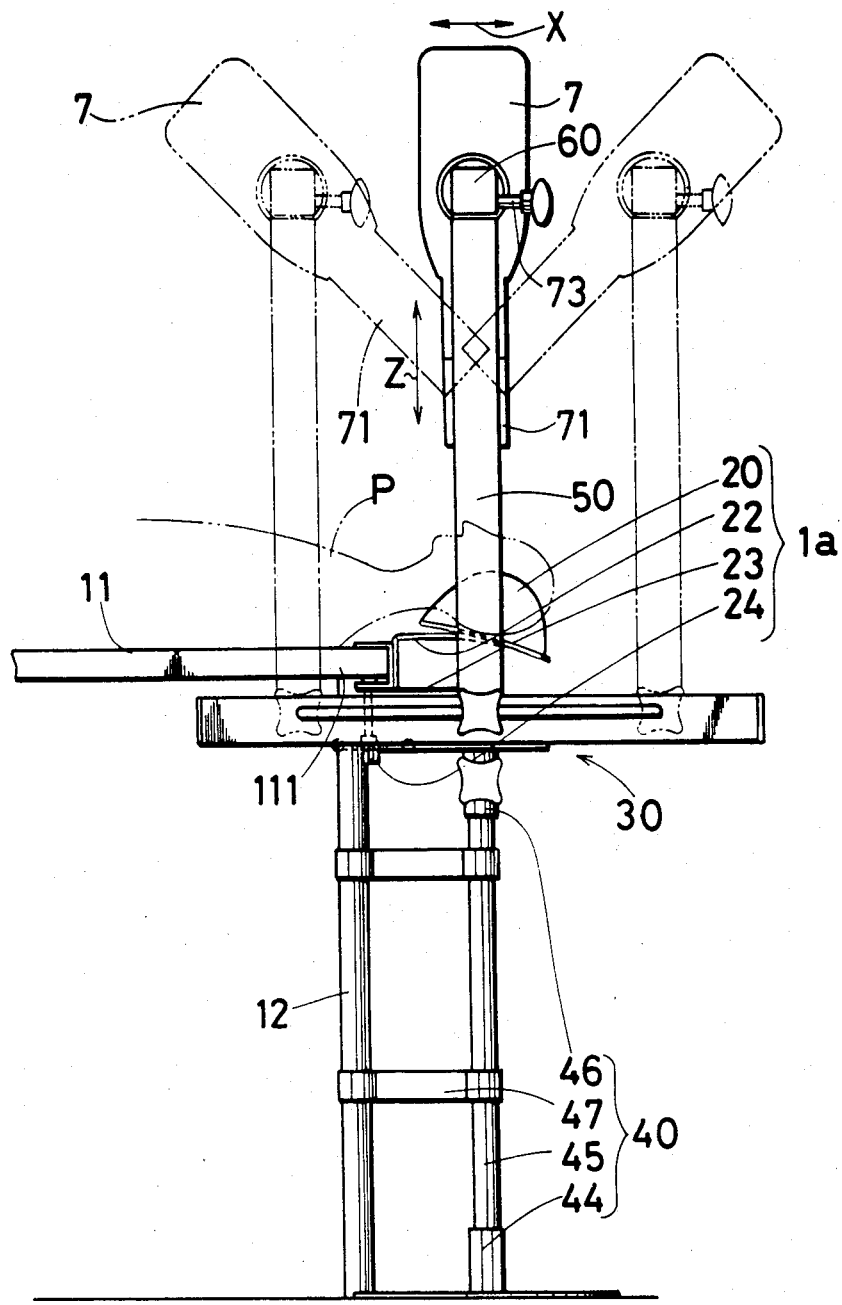
FIG. 6 is a diagrammatic view illustrating a state of use of an X-ray head in the second embodiment.

In a second embodiment shown in FIGS. 4 and 6, the support 10 for X-ray head 7 includes a slide guide 30 connected by a fixing means 40 to the treatment bed 1 and disposed horizontally in a longitudinal direction X, a vertical strut 50 fitted slidably into the slide guide 30 in the longitudinal direction X and expansible in a vertical direction Z, and a slider 60 fitted into a guide member 510 disposed on the top of the strut 50 and slidable in the direction of width Y. The X-ray head 7 is mounted to the slider 60.

Figure 5:
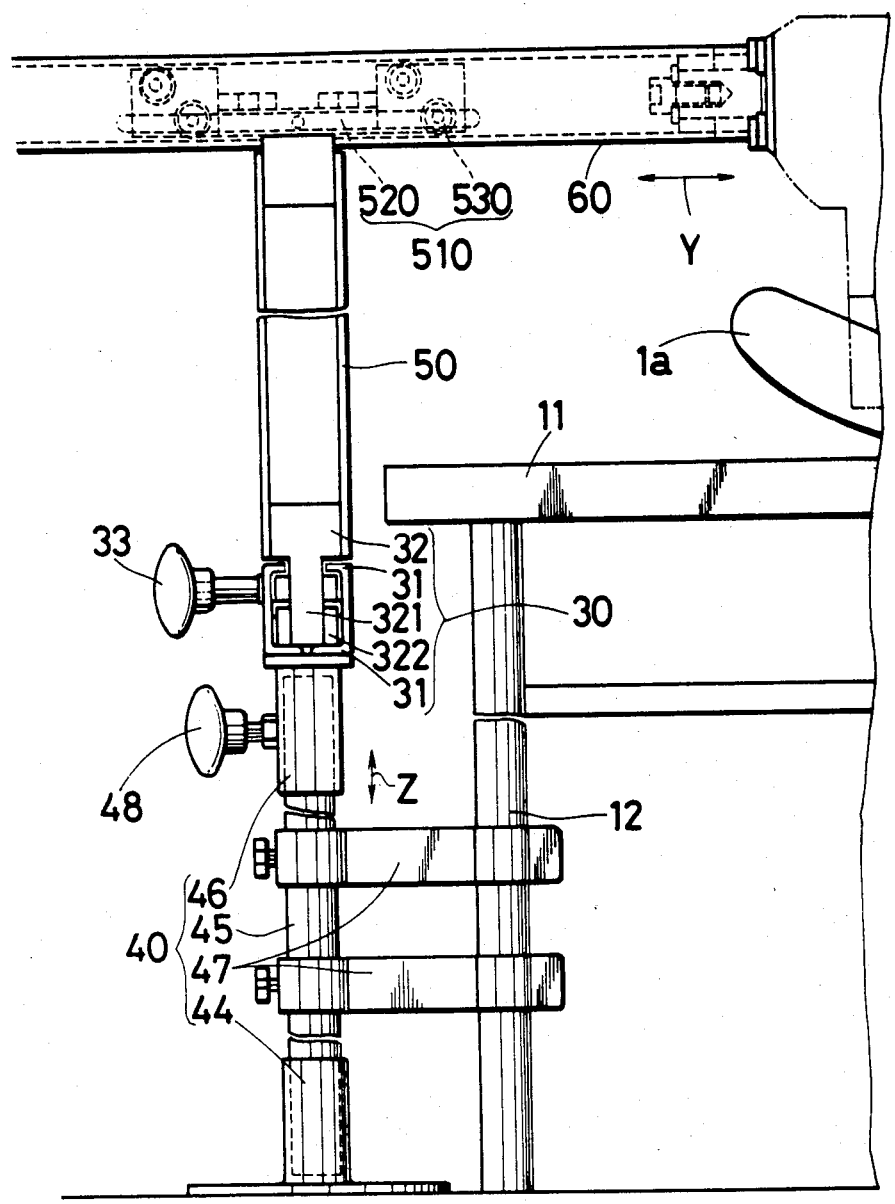
FIG. 5 is a diagrammatic view, broken away in part, of the structure of a guide element disposed on the top of a support in the second embodiment.

Incidentally, the treatment bed 1 shown in the second embodiment is generally used as a study desk in schools, so that the embodiment shown may be adapted for use in combination with a study desk. A headrest 1a, as shown in FIG. 6, includes a support plate 20 for placing the rear part of the head of a patient P thereon, the plate 20 being coupled through a support arm 22 to a U-shaped clamping frame 23. The calmping frame 23 is fitted over the end edge 111 of the upper board 11 of the bed 1 and is fixed to the board 11 by tightening a clamping fixture 24 threadedly mated with the frame 23 from below. In FIGS. 4 to 6, a slide guide 30 for controlling the movement of the X-ray head 7 in the longitudinal direction X of the bed 1 is fixed by a fixing means 40 on a slide guide locking means 46 adjacent of one side of the bed 1. The fixing means 40 includes an installation stand 44, a tubular pole 45 detachably fitted into the stand 44, more than at least a pair of connecting means 47 for detachably connecting and fixing the pole 45 to a leg 12 of the bed 1, and a slide guide locking means 46 detachably and vertically slidably fitted over the top of the pole 45. The numeral 48 designates a clamping screw for the slide guide locking means 46. The slide guide mechanism as shown in FIG. 5 uses one in which a slider 321 integral with a sliding body 32 and rollers 322 are used and which is highly accurate and has little play. The mechanism may permit the application of the slider mechanism which is disclosed in the Japanese Utility Model Application No. 094506/1981 filed by the present applicant and which includes rollers having antiwear measures taken therefor, and such other mechanisms in which are used linear rotary bearings. The sliding body 32 is slidably incorporated in a guide mechanism 31 made of hollow square pillars and having on the upper side thereof an opening 311 for sliding movement. A strut 50 is connected to the sliding body 32 so as to permit vertically slidable detachment from the body 32 with respect to the sliding of the strut 50 in the longitudinal direction X of the bed 1. The strut 50 is fixed in its position by clamping and fixing the sliding body 32 to the slide guide mechanism 31 by tightening a screw clamping fixture 33 is a specified position. A guide assembly 510 of the strut 50, which guides the slider 60 in a direction normal to the longitudinal direction X of the bed 1, which means the direction in which the sliding body 32 slides, namely in the direction of width Y of the desk, is of the same construction as the sliding body 32 and includes a horizontal block 520 and rollers 530, the block 520 being fixed to the top of the strut 50 and the rollers 530 being rotatably mounted on the block 520.

The X-ray head 7 containing therein an X-ray generator and a control device is detachably connected through a rotational angle indicator dial 72 to the end 601 of the slider 60. The X-ray head 7 as shown in FIG. 6 can swing through a maximum angle of 45° about a connection pin 73 back-and-forth with respect to the axis of the irradiation tube 71. The angle of swing is indicated by the rotational angle indicator dial 72. The expansible irradiation tube 71 is fixed to the underside of the head 7. Adjustment of the length of the tube 7 controls the distance between the focus and the skin in proportion to the tube voltage of the X-rays generated. The same is true of the irradiation tube and X-ray head 7 in the first embodiment. Because the length of the strut 50 is so selected as to position the X-ray head 7 at a specified distance from the upper board 11 of the bed 1, the position of the irradiation tube 71 with respect to the headrest 1a is held in a completely established relation. The slide guide mechanism 31, slider 32, strut 50 and slider 60 are made of hollow aluminum members, respectively so as to save labor when carrying, and enable the mechanism 31, strut 50 and slide 60 to be divided into suitable sizes, respectively by taking off the end plates 31a and 60a from the members 31 and slider 60 and to store the thus disassembled parts in a storing case. A control box 9 is mounted in an easy-to-operate position.

It will become apparent from the description above that the second embodiment of the above construction makes it possible to select the correct position for the irradiation tube 71 with respect to the mouth M by a support adjustable lengthwise with respect to the three-dimensional directions X, Y and Z in the same manner as in the first embodiment. Especially in the second embodiment, even one person can carry separately the hollow members constituting the support 10 which are disassembled from the bed 1 so as to reassemble the same on the site, and accordingly the invention is very convenient for dental X-ray photographing in districts with difficult access such as out-of-the-way and secluded places among the mountains.

We claim:

1. A simple mounting structure in a dental X-ray apparatus for use in combination with a substantially horizontal treatment bed to position an irradiation tube of an X-ray head in a specified and repeatable position with respect to the mouth region of a patient with his head placed on a headrest of the bed, said structure being characterized in that the structure comprises said treatment bed, an X-ray head support connected to one side of said bed and comprising an assembly of a plurality of hollow tubes adjustable in length in the three-dimensional directions of length, width and height of said head, and an X-ray head mounted at the end of said support and swingable in a back-and-forth direction with respect to an axis of said irradiation tube, said irradiation tube being mounted on said X-ray head and movable toward and away from said mouth region.

2. A structure according to claim 1, wherein said support comprises a storing track mounted on one side of said treatment bed along the longitudinal direction of the bed, a slider slidably inserted into said track with respect to the longitudinal direction of the track, a stand pole telescopable tube connected in a vertical direction to the end of said slider, a stand pole slidably inserted into said telescopable tube in the vertical direction and movable around the axis of the tube and having a horizontally curved portion on the top thereof, and an operating tube slidably fitted into said curved portion with respect to the direction of width, whereby when the X-ray head is attached to said operating tube and when said tube and said stand pole are telescoped into said stand pole telescopable tube and when said slider is telescoped into said storing track, said X-ray head and said support are telescoped into one side of said treatment bed.

3. A structure according to claim 2, wherein said stand pole telescopable tube and said stand pole are provided with stoppers for locking said tube and stand pole in position.

4. A structure according to claim 3, wherein said stand pole comprises a vertical pole and a curved pole, said curved pole being slidable in the direction of height with respect to said vertical pole and being rotatably inserted into said vertical pole around the axis thereof and having an about 90° curved portion, said vertical pole and said curved pole including a screw stopper for locking the vertical and curved poles in position at the point at which one is fitted into the other.

5. A structure according to claim 2, wherein said stand pole telescopable tube is equipped with a control box for operating X-ray photographing.

6. A structure according to claim 2, wherein said slider and said stand pole telescopable tube are connected to each other through a horizontal connecting block.

7. A structure according to claim 1, wherein said X-ray head support comprises a slide guide connected by fixing means to said treatment bed and disposed horizontally in the longitudinal direction of the bed, a vertical strut slidably inserted into said guide in the longitudinal direction thereof and expansible in the direction of height, and a slider inserted into a guide means attached to the top of said strut and slidable in the direction of width, said X-ray head being attached to said slider.

8. A structure according to claim 7, wherein said fixing means comprises an installation stand, a pole detachably fitted into said stand, more than at least a pair of connecting blocks for detachably connecting and fixing said pole to a leg of said treatment bed, and a slide guide locking means detachably and slidably fitted over the top of said pole.

9. A structure according to claim 8, wherein said guide means comprises a horizontal block fixed to a top of said stut and rollers rotatably mounted on said horizontal block.

10. A structure according to claim 9, wherein said guide means comprises two horizontal slide guide rods supported by horizontal support rods in a relation normal to the slide rods.

* * * * *